United States Patent [19]
He et al.

[11] Patent Number: 6,141,398
[45] Date of Patent: Oct. 31, 2000

[54] PROTOCOL DRIVEN IMAGE RECONSTRUCTION, DISPLAY, AND PROCESSING IN A MULTISLICE IMAGING SYSTEM

[75] Inventors: Hui David He, Waukesha; Stanley H. Fox; Sholom M. Ackelsberg, both of Brookfield, all of Wis.

[73] Assignee: General Electric Company, Milwaukee, Wis.

[21] Appl. No.: 09/139,438

[22] Filed: Aug. 25, 1998

[51] Int. Cl.$^7$ .......................................... A61B 6/03
[52] U.S. Cl. .................................. 378/4; 378/901
[58] Field of Search ............... 378/4, 8, 15, 62, 378/901

[56] References Cited

U.S. PATENT DOCUMENTS

| 4,352,021 | 9/1982 | Boyd et al. | 378/12 |
| 5,018,178 | 5/1991 | Katsumata | 378/91 |
| 5,231,651 | 7/1993 | Ozaki et al. | 378/4 |
| 5,430,784 | 7/1995 | Ribner et al. | 378/19 |
| 5,668,845 | 9/1997 | Migita | 378/4 |
| 5,970,112 | 10/1999 | Hsieh | 378/8 |

FOREIGN PATENT DOCUMENTS

| 0 662 305 A1 | 7/1995 | European Pat. Off. |
| WO 98/32371 | 7/1998 | WIPO |

*Primary Examiner*—David V. Bruce
*Attorney, Agent, or Firm*—Armstrong Teasdale; Christian G. Cabou; Phyllis Y. Price

[57] ABSTRACT

A scalable multislice system configured to generate multiple streams of image data with different image quality characteristics prospectively and simultaneously is described. Such capability enables improving existing clinical diagnosis and also enables use of clinical application protocol driven method for image reconstruction and display as well as image analysis. More specifically, with the scalable multi-slice imaging system, multiple rows (>2) of x-ray scan data along the patient's long axis are simultaneously acquired. Multiple protocols are "pre-built" based on specific applications to determine image slice thickness, image reconstruction filter, display method, e.g., field of view, filming requirement and image archiving requirement, prospectively. Multiple image sets with different slice thickness, different reconstruction methods, different display model—axial, 3D or reformat which are pre-determined by the protocol used can then be displayed.

25 Claims, 3 Drawing Sheets

HELICAL

THICKNESS (mm): | 1.25 | 2.50 | 3.75 | 5.00 | 7.50 | 10.00 |

SCAN MODE: HI-Q | HI-SPEED

SPEED (mm/rot): 3.75 | 7.50 | 11.25 | 15.00 | 22.50 | 30.00

AXIAL

THICKNESS (mm): 1.25 | 2.50 | 3.75 | 5.00 | 7.50 | 10.00

NUMBER OF IMAGES PER ROTATION: 11 | 21 | 41

FIG. 3

PROTOCOL DRIVEN IMAGE RECONSTRUCTION, DISPLAY, AND PROCESSING IN A MULTISLICE IMAGING SYSTEM

BACKGROUND OF THE INVENTION

This invention relates generally to imaging and, more particularly, to scalable multislice imaging systems.

In at least some imaging systems generally referred as computed tomography (CT) systems, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

Dual (two) slice CT systems are known, but at least some of the commercially available dual slice systems have a number of limitations, including balancing scanning speed and z-axis resolution (e.g., as scanning speed increases, z-axis resolution decreases), image quality associated with image reconstruction processing, and flexibility, e.g., such systems cannot collect more than 2 slices of data. Particularly, the known commercially available dual slice systems are not scalable in that such dual slice systems cannot be configured to collect more than two slices of data.

In addition, for many clinical applications of CT imaging, CT images in different slice thickness, different cross-sectional orientation, and different 3D display models must be examined for accurate diagnosis. In many cases, multiple CT scans and image reconstructions are required for such diagnosis. As a result, diagnosis can be very time consuming and sometimes can result in delay of treatment to patients.

It would be desirable to provide a multislice CT system that can be used to collect one, two or more slices of data, and is readily configurable to perform the scans and reconstructions necessary for accurate diagnosis. It also would be desirable to reduce the complexity and time required in performing such scans and reconstructions.

BRIEF SUMMARY OF THE INVENTION

These and other objects may be attained by a scalable multislice system configured to generate multiple streams of image data with different image quality characteristics prospectively and simultaneously. Such capability enables improving existing clinical diagnosis and also enables use of clinical application protocol driven method for image reconstruction and display as well as image analysis. More specifically, with the scalable multislice imaging system, multiple rows (>2) of x-ray scan data along the patient's long axis are simultaneously acquired. For example, in the axial multi-slice scan mode, multiple rows of scan data can be processed before image reconstruction, and are used to produce either (a) multiple thin slices for maximum z-axis resolution or (b) reduced number of thicker image slices with reduced image artifacts in comparison to conventional CT scanners. As described below in detail, in a data acquisition mode of 4×2.5 mm, one 10 mm image, two 5 mm images or four 2.5 mm images can be generated per gantry rotation from the same raw scan data. The 2.5 mm images provide better z-axis resolution. The 10 mm images provide reduced partial volume artifact compared with a single slice CT 10 mm slice. In helical multi-slice scanning, multi-slice helical image reconstruction algorithms enable generation of multiple image sets having different z-axis resolution, both prospectively and retrospectively. As an example, at the table speed of 30 mm/rotation, images of 5 to 10 mm slices thickness can be generated.

Accordingly, multiple protocols are "pre-built" based on specific applications to determine image slice thickness, image reconstruction filter, display field of view, filming requirement and image archiving requirement, prospectively. Multiple image sets with different slice thickness, different reconstruction methods, different display model—axial, 3D or reformat which are pre-determined by the protocol used can then be displayed.

For example, in a CT angiography (CTA) application, both cross-section images and 3D/reformat models of major vessels are required. A protocol specific for CTA can be defined as follows.

acquire a helical scan data set in the 4×1.25 mm mode preprocess raw scan data reconstruct two set of images, prospectively: one set of 2.5 mm cross-sectional image for diagnosis, and another set of 1.25 mm images for building 3D or reformat CT angiography models.

display, film, and archive both the axial images and 3D/reformat model

Of course, protocols for many other types of applications can be created and stored in the CT system for use by the operator.

The above described image reconstruction and display methods and apparatus facilitate improving imaging productivity, reducing the number of CT scans, and decreasing diagnosis cycle time. Such methods and apparatus may also reduce the number of unwanted images for viewing, filming and archiving, and have the capability of producing 3- or 4-dimensional images with high z-axis resolution information for multiple clinical purposes.

BRIEF DESCRIPTION OF THE DRAWINGS

FIG. 3 is an exemplary embodiment of a scan user interface than can be used in conjunction with the system illustrated in FIGS. 1 and 2.

DETAILED DESCRIPTION OF THE INVENTION

The present invention is directed, in one aspect, to protocol driven image reconstruction, display and archiving, and in another aspect to a method for multislice image generation. The invention can be practiced in connection with many different types of imaging systems, and is not limited to practice to any one type of system. Set forth herein, however, is a detailed description of an exemplary multislice CT system, and although such CT system is described in detail below, it should be understood that the present invention is not limited to practice with such system.

Figure 1:
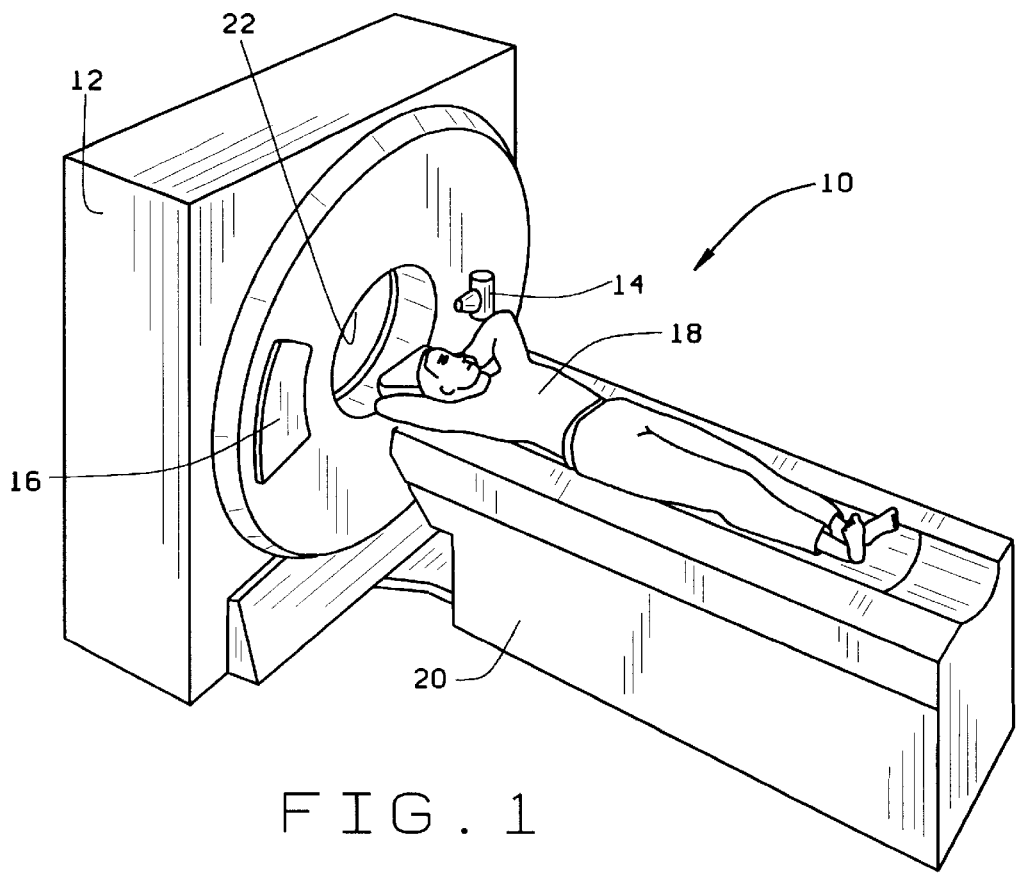
FIG. 1 is a pictorial view of a CT imaging system.

More particularly, and referring to FIG. 1, an exemplary computed tomography (CT) imaging system 10 in accordance with one embodiment of the present invention is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
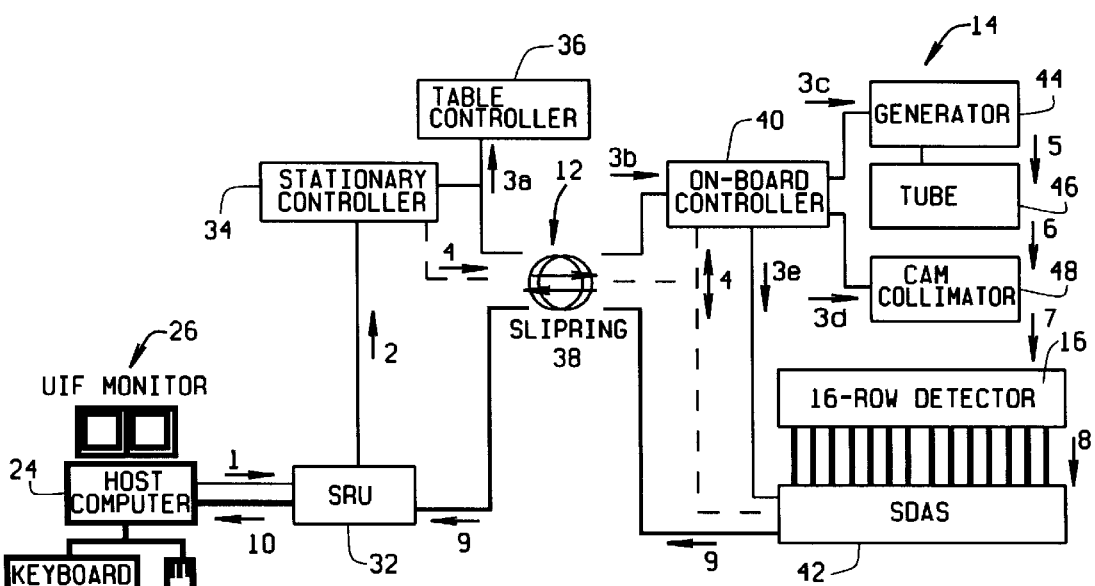
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system (described below), and a scan data correction digital signal processing board for performing preprocessing, which is known in the art. SRU 32 further includes an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. Slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in one specific embodiment, includes forty eight interchangeable converter cards to support four row data acquisition. For two row data acquisition, twenty four cards could be used. In one specific embodiment, there are sixty four input channels per converter card and 1408 Hz sampling can be performed. SDAS 42 also includes a front-end pre-amplifier for amplifying the signals. Further details regarding SDAS are set forth below.

On-board controller 40 controls operation of x-ray source 14 and operation of SDAS 42. X-ray source 14 includes a high voltage generator 44 coupled to an x-ray tube 46. Tube 46 may, for example, be the tube known in the art is the Gemini-1 tube and currently utilized in at least some CT system commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to SDAS 42.

In FIG. 2, data flow is illustrated by bold lines, control flow is illustrated by normal lines, and real-time control flow is illustrated by dotted lines. The numeric identifiers associated with the flows are set forth below.

1: scan and reconstruction prescription from operator
2: scan prescription to "master" controller
3: scan parameters distributed
   3a: table position
   3b: rotating parameters
   3c: kV and mA selections
   3d: x-ray beam collimation and filter selections
   3e: detector slice thickness and SDAS gain selections
4: real-time control signals during scanning
5: high voltage
6: un-collimated x-ray beam
7: collimated x-ray beam
8: analog scan data
9: digital scan data
10: patient images Rotation of gantry 12 and the operation of x-ray source 14 are governed by controller 34. On-board controller 40, under the control of stationary controller 34, provides power and timing signals to x-ray source 14. SDAS 42 samples analog data from detector 16 and converts the data to digital signals for subsequent processing. SRU 32 receives sampled and digitized x-ray data from SDAS 42 and performs high speed image reconstruction. The reconstructed image is applied as an input to computer 24 which stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (FIG. 1).

Generally, the above described CT system is operable to collect 1, 2 or more slices data. Axial and helical scans can be performed with the system, and cross section images of a scanned object can be processed, reconstructed, displayed and/or archived. Scalable axial image reconstruction and display refers, for example, to selectability of the image thickness, number of slices, and number of images to be displayed. Further, the system is not limited to practice with any one particular image reconstruction algorithm, and it is contemplated that many different reconstruction algorithms can be utilized. Exemplary algorithms are set forth in U.S. Pat. Nos. 5,469,487, 5,513,236, 5,541,970, 5,559,847, and 5,606,585, and in co-pending U.S. patent application Ser. Nos. 08/561,382 (filed Nov. 21, 1995), 08/779,961 (filed Dec. 23, 1996), and 08/797,101 (filed Nov. 26, 1997), all of which are assigned to the present assignee, and all of which are incorporated herein, in their entirety, by reference.

In the axial multi-slice scan mode, multiple rows of scan data can be processed before image reconstruction, and the data can be used to produce either multiple thin slices or a reduced number of thicker slices with reduced image artifact. In addition, images with thicker slice thicknesses can be later reconstructed retrospectively into thinner slices of images based on clinical diagnosis needs. As a result, the number of unwanted images for viewing, filming, and archiving is reduced. In addition, high z-axis resolution images can be later reconstructed for patient diagnosis.

Exemplary axial multi-slice modes are set forth below in Table 1.

TABLE 1

| Acquisition<br>Image Thickness & Mode | | Retrospective Reconstruction<br>Image Thickness Available |
|---|---|---|
| 1.25 mm | 4i | 1.25, 2.5, 5 mm |
| 2.5 mm | 2i | 1.25, 2.5, 5 mm |
| 2.5 mm | 4i | 2.5, 5, 10 mm |
| 3.75 mm | 4i | 3.75, 7.5 mm |
| 5 mm | 1i | 1.25, 2.5, 5 mm |
| 5 mm | 2i | 2.5, 5, 10 mm |
| 5 mm | 4i | 5, 10 mm |
| 7.5 mm | 2i | 3.75, 7.5 mm |
| 10 mm | 1i | 2.5, 5, 10 mm |
| 10 mm | 2i | 5, 10 mm |

As one specific example, and for an axial mode acquisition for a 2.5 mm image thickness in the 2i mode, several retrospective reconstruction options that can be selected. For example, 4 images having a slice thickness of 1.25 mm can be reconstructed, 2 images having a slice thickness of 2.5 mm can be reconstructed, and 1 image having a slice thickness of 5 mm can be reconstructed. Accordingly, more images (e.g., 4 images) having a thinner slice thickness can be retrospectively reconstructed than the mode (i.e., 2i) in which the scan was performed. In addition, fewer images (e.g., 1 image) having a thicker slice thickness can be retrospectively reconstructed than the mode in which the scan was performed.

Further, and with respect to archiving images, the system enables storage of fewer images which require less storage space. For example, if 20 mm of patient anatomy is scanned in the 2i mode, 80 images can be generated. Storing 80 images for 20 mm of patient anatomy requires a large amount of memory. It is often the case that high resolution is not required for the entire 20 mm of patient anatomy. For example, it may be that only about 5 mm of the anatomy requires such high resolution. Using the data collected in 2.5 mm thickness 2i mode scan, the operator can retrospectively reconstruct images having a thickness of 5 mm for the majority of the anatomy, and thinner image slices (e.g., 1.25 mm) only at the locations where higher resolution is required. Using this retrospective reconstruction, the number of images to be archived can be significantly reduced.

Selection of the above described retrospective reconstruction is provided through the user interface, and possible because the scan data is collected using a multislice detector which is described below in more detail. With the thin slice scan data available, the operator can select from many different slice thicknesses when performing retrospective reconstruction.

In the helical multi-slice scan mode, multiple combinations of patient table speed and x-ray beam and detector collimations, enable generation of images having different z-axis resolution can be produced. For example, at the table speed of 30 mm/rotation, images of 5–10 mm slices can be generated. Thicker slice (such as 10 mm) images can be generated prospectively, which provides the benefit of a reduced number of images and reduced image reconstruction time. At a later time, thinner slice images can be generated retrospectively using the same data. Such thinner slice images may be necessary depending on the clinical application needs and can be generated without rescanning the patient.

Exemplary helical multi-slice modes are set forth below in Table 2.

TABLE 2

| Table Speed (mm/rotation) | | Retrospective Reconstruction |
|---|---|---|
| Hi-Q Scan Mode | Hi-Speed Scan Mode | Image Thicknesses Available |
| 3.75 | 7.5 | 1.25, 2.5 mm |
| 7.5 | 15 | 2.5, 3.75, 5 mm |
| 11.25 | 22.5 | 3.75, 5, 7.5 mm |
| 15 | 20 | 5, 7.5, 10 mm |

For example, in a high quality image (Hi-Q) scan mode of 3.75 mm/rotation (i.e., the patient table moves 3.75 mm for each gantry rotation), or in a high speed (Hi-Speed) scan mode of 7.5 mm /rotation, images having slice thicknesses of 1.25 mm and 2.5 mm can be reconstructed retrospectively. As with the axial multi-slice mode, many other alternatives are possible depending upon the particular construction of the system components. Again, such flexibility in retrospective reconstruction provides many advantages including enabling the generation of images having the necessary resolution yet reducing the memory necessary for storing the desired images.

FIG. 3 is an exemplary embodiment of a scan user interface than can be used in conjunction with the system illustrated in FIGS. 1 and 2. The interface is implemented using an instruction set stored in host computer 24 (FIG. 2) and displayed on the host computer monitor. At the scan user interface, an operator selects the scan mode, i.e., helical or axial, as well as the various scan parameter associated with each mode. The selections are made, for example, by the user simply touching the desired area corresponding to the desired parameters. Touch sensitive interfaces are well known. Of course, many other types of interfaces could be used, and the interface illustrated in FIG. 3 is only an exemplary interface.

In the helical mode, the operator selects the desired slice thickness, the scan mode, and the scan speed. The "Hi-Q" scan corresponds to a high image quality scan and the "Hi-Speed" scan corresponds to a fast patient table speed, as described above in connection with Table 2. In the axial scan, the operator selects the desired slice thickness and the number of images to be generated per rotation.

The above described multi-slice CT system provides scalable scan management, control, and image reconstruction processes, and scalable image display and analysis. With such system, an operator can readily and simply select the desired number of slices and the slice thickness for images to be displayed. In addition, increased patient scan speed, improved image quality, and reduced x-ray tube loading are achieved. Additional details regarding the above described multislice imaging system are set forth in co-pending U.S. patent application Ser. No. (15-CT-4641), entitled Scalable Multislice Imaging System, which is assigned the present assignee and hereby incorporated herein, in its entirety, by reference.

As explained above, typical CT patient scans are done in either axial mode (patient table stop, scan and then move) or in helical mode (patient table moves continuously during scan). With the above described scalable multi-slice CT system, multiple rows (>2) of x-ray scan data can be acquired along the patient's long axis, simultaneously. In the axial multi-slice scan mode, multiple rows of scan data can be processed before image reconstruction, and are used to produce either (a) multiple thin slices for maximum z-axis resolution or (b) reduced number of thicker image slices with reduced image artifacts in comparison to conventional CT scanners. For example, and as explained above, in a data acquisition mode of 4×2.5 mm one can produce one 10 mm image, two 5 mm images, or four 2.5 mm images per gantry rotation from the same raw scan data. The 2.5 mm images provide better z-axis resolution. The 10 mm images provide reduced partial volume artifact compared with a single slice CT 10 mm slice.

In helical multi-slice scanning, multi-slice helical image reconstruction algorithms enable generation of multiple image sets having different z-axis resolution both prospectively and retrospectively. As an example, at the table speed of 30 mm/rotation, images of 5 to 10 mm slices thickness can be generated.

By using predefined protocols in connection with the above described system, a system operator can simultaneous view and analyze CT images with different diagnosis characteristics. The entire process is driven by the protocols, which are unique for each clinical applications.

Figure 4:
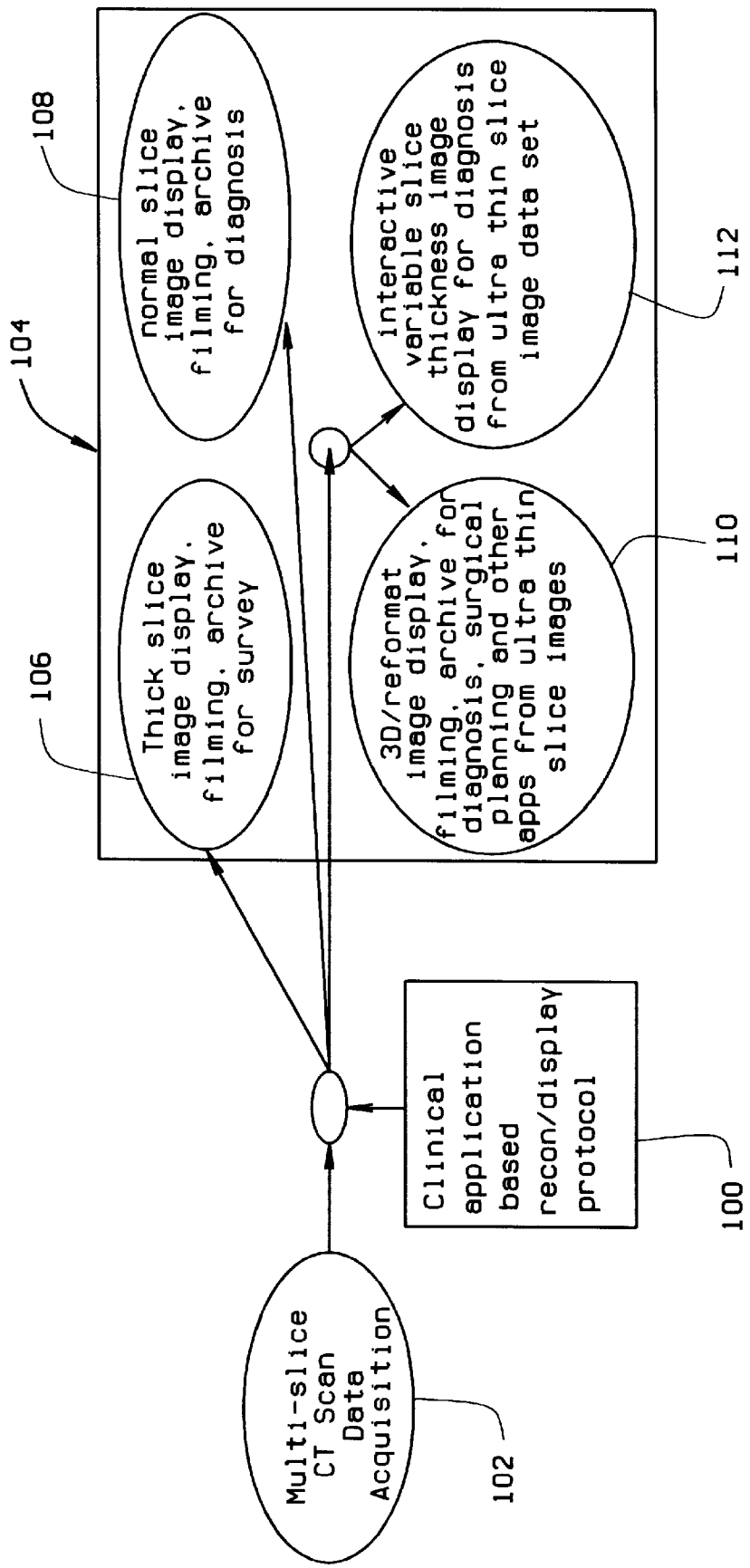
FIG. 4 is a logic diagram of protocol driven image reconstruction, display, analysis, and archiving.

More specifically, and referring to FIG. 4 which is a logic diagram of protocol driven image reconstruction, display, analysis, and archiving, multiple protocols 100 are predefined, or prebuilt, based on specific applications to determine image slice thickness, image reconstruction filter, display field of view, filming requirement and image archiving requirement, prospectively. The multislice data acquisition 102 is then executed in accordance with the protocols. Images are then displayed, filmed, and/or archived 104 in accordance with the protocols. For example, a thick slice image 106, and normal slice image 108, and 3D/reformat image 110, and/or an interactive variable slice thickness image 112, as explained below in more detail, can be generated. That is, multiple image sets with different slice thickness, different reconstruction methods, different display model—axial, 3D or reformat which are pre-determined by the protocol used can be displayed.

With respect to a variable slice thickness image, and in an axial image display mode, multiple ultra thin slice cross sectional images are weighted and then superimposed to form a new image with the desired slice thickness. This process is described by:

$$I(x,y)_s = \Sigma W_i * I(x,y)_i$$

where $I(x,y)_s$ is the resulted image pixel values at location x and y, $W_i$ is the weighting factor determined by the final image slice thickness and sub-slice image thickness, and $I(x,y)_i$ is the pixel values at x and y for the sub-slice images.

With respect to an exemplary protocol, and in a CT angiography (CTA) application, both cross-section images and 3D/reformat models of major vessels are required. A protocol specific for CTA can be defined as follows.

acquire a helical scan data set in the 4×1.25 mm mode
preprocess raw scan data
reconstruct two sets of images, prospectively: one set of 2.5 mm cross-sectional image for diagnosis, and another set of 1.25 mm images for building 3D or reformat CT angiography models.
display, film, and archive both the axial images and 3D/reformat model Another exemplary protocol relates to a head trauma study. A protocol specific for a head trauma study can be defined as follows.

acquire axial scan data in the 4×2.5 mm mode
preprocess raw scan data
reconstruct three sets of cross-sectional images with slice thickness of 2.5 mm, 5 mm and 10 mm for different portions of the head. Different reconstruction algorithms may be used for different sets.
display all three image sets simultaneously on the console with different preset display field-of-view and widow/levels The above examples illustrate the protocol driven process for CT image acquisition, display and diagnosis. Multiple scan, reconstruction, display, image processing, filming and archiving parameters can be used in building the protocols which are not limited by the fields demonstrated in the examples. The protocols are stored, for example, in SRU 32 and selected by the operator via host computer 24 (FIG. 2).

Use of such protocols may facilitate improving CT imaging productivity, reducing the number of CT scans, and decreasing diagnosis cycle time. Use of such protocols may also reduce the number of unwanted images for viewing, filming and archiving. Further, such protocols can be used in connection with generations of 3- or 4-dimensional images with high z-axis resolution information for multiple clinical purposes. The protocols can be applied to many different applications including, but not limited to, CT neuro imaging, CT angiography, renal donor survey, pulmonary embolism, CT trauma imaging, whole body CT survey, lung disease screening and many other CT diagnosis imaging applications.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What claimed is:

1. A protocol for defining operations performed by a multislice imaging system, said protocol comprising designations for at least one of slice thickness, image reconstruction filter, display method, filming requirement and image archiving requirement, and further including designations for reconstruction of images from multiple rows of scan data, the reconstructed images having thicknesses varying in accordance with a resolution requirement.

2. A protocol in accordance with claim 1 wherein said protocol designates at least one of CT neuro imaging, CT angiography, renal donor survey, pulmonary embolism, CT trauma imaging, whole body CT survey, and lung disease screening.

3. A protocol in accordance with claim 1 wherein said designations for reconstruction of images having varying thicknesses include designations for retrospective reconstruction of images.

4. A protocol in accordance with claim 3 wherein said protocol includes an image archiving requirement, and said image archiving requirement includes archival of images of a scanned portion of a patient anatomy as images having different thicknesses at different locations of the patient anatomy in accordance with a resolution requirement, to reduce a number of images to be archived.

5. A protocol in accordance with claim 1 wherein said protocol designates an axial image display mode, weighting multiple ultra thin slice cross sectional images, and generating an image with a desired slice thickness.

6. A protocol in accordance with claim 5 wherein said image is generated in accordance with:

$$I(x,y)_s = \Sigma W_i * I(x,y)_i$$

where $I(x,y)_s$ is the resulted image pixel values at location x and y, $W_i$ is the weighting factor determined by the final image slice thickness and sub-slice image thickness, and $I(x,y)_i$ is the pixel values at x and y for the sub-slice images.

7. A protocol in accordance with claim 1 wherein said protocol designates a head trauma study and comprises instructions for:

acquiring axial scan data sets;

preprocessing raw scan data;

reconstructing sets of cross-sectional images with different slice thickness for different portions of the head; and displaying the image sets simultaneously.

8. A multislice imaging system programmed to execute a scan in accordance with a protocol, said protocol comprising designations for at least one of slice thickness, image reconstruction filter, display method, filming requirement, and image archiving requirement, and further including designations for reconstruction of images from multiple rows of scan data, the reconstructed images having thicknesses varying in accordance with a resolution requirement.

9. A system in accordance with claim 8 wherein said designations for reconstruction of images having varying thicknesses include designations for retrospective reconstruction of images.

10. A system in accordance with claim 9 wherein said system includes an image archiving requirement, and said image archiving requirement includes archival of images of a scanned portion of a patient anatomy as images having different thicknesses at different locations of the patient anatomy in accordance with a resolution requirement, to reduce a number of images to be archived.

11. A system in accordance with claim 8 wherein said protocol designates a head trauma study and comprises instructions for:

acquiring axial scan data sets;

preprocessing raw scan data;

reconstructing sets of cross-sectional images with different slice thickness for different portions of the head; and displaying the image sets simultaneously.

12. A system in accordance with claim, 8 wherein said protocol designates an axial image display mode, weighting multiple ultra thin slice cross sectional images, and generating an image with a desired slice thickness.

13. A system in accordance with claim 12 wherein said image is generated in accordance with:

$$I(x,y)_s = \Sigma W_i * I(x,y)_i$$

where $I(x,y)_s$ is the resulted image pixel values at location x and y, $W_i$ is the weighting factor determined by the final image slice thickness and sub-slice image thickness, and $I(x,y)_i$ is the pixel values at x and y for the sub-slice images.

14. A system in accordance with claim 8 wherein said protocol designates at least one of CT neuro imaging, CT angiography, renal donor survey, pulmonary embolism, CT trauma imaging, whole body CT survey, and lung disease screening.

15. A multislice imaging system programmed to generate an image in accordance with:

$$I(x,y)_s = \Sigma W_i * I(x,y)_i$$

where $I(x,y)_s$ is the resulted image pixel values at location x and y, $W_i$ is the weighting factor determined by the final image slice thickness and sub-slice image thickness, and $I(x,y)_i$ is the pixel values at x and y for the sub-slice images, and to perform a scan in accordance with a predefined protocol designating at least one of slice thickness, image reconstruction filter, display method, filming requirement, and image archiving requirement, and further including designations for reconstruction of images from multiple rows of scan data, the reconstructed images having thicknesses varying in accordance with a resolution requirement.

16. A system in accordance with claim 15 configured to acquire and pre-process multiple rows of raw scan data, and to generate, from the scan data, multiple streams of images having different image quality characteristics prospectively.

17. An system in accordance with claim 16 configured to prospectively generate image slices from the scan data having a first thickness, and to retrospectively generate image slices from the same scan data having a second thickness less than the first thickness.

18. A system in accordance with claim 15 wherein said protocol designates a head trauma study and comprises instructions for:

acquiring axial scan data sets;

preprocessing raw scan data;

reconstructing sets of cross-sectional images with different slice thickness for different portions of the head; and displaying the image sets simultaneously.

19. A system in accordance with claim 15 wherein said protocol designates an axial image display mode, weighting multiple ultra thin slice cross sectional images, and generating an image with a desired slice thickness.

20. A system in accordance with claim 15 wherein said protocol designates at least one of CT neuro imaging, CT angiography, renal donor survey, pulmonary embolism, CT trauma imaging, whole body CT survey, and lung disease screening.

21. A system in accordance with claim 15 wherein said designations for reconstruction of images having varying thicknesses include designations for retrospective reconstruction of images.

22. A system in accordance with claim 21 wherein said protocol includes an image archiving requirement, and said image archiving requirement includes archival of images of a scanned portion of a patient anatomy as images having different thicknesses at different locations of the patient anatomy in accordance with a resolution requirement, to reduce a number of images to be archived.

23. A protocol for defining operations performed by an imaging system, said protocol comprising designations for at least one of slice thickness, image reconstruction filter, display method, filming requirement and image archiving requirement wherein said protocol designates CT angiography and comprises instructions for:

acquiring a helical scan data set;

preprocessing raw scan data;

reconstructing sets of images, prospectively; and displaying images.

24. A multislice imaging system programmed to execute a scan in accordance with a protocol, said protocol comprising designations for at least one of slice thickness, image reconstruction filter, display method, filming requirement and image archiving requirement wherein said protocol designates CT angiography and comprises instructions for:

acquiring a helical scan data set;

preprocessing raw scan data;

reconstructing sets of images, prospectively; and displaying images.

25. A multislice imaging system programmed to generate an image in accordance with $$I(x,y)_s = \Sigma W_i * I(x,y)_i$$

where $I(x,y)_s$ is the resulted image pixel values at location x and y, $W_i$ is the weighting factor determined by the final image slice thickness and sub-slice image thickness, and $I(x,y)_i$ is the pixel values at x and y for the sub-slice images, and wherein said protocol designates CT angiography and comprises instructions for:

acquiring a helical scan data set;

preprocessing raw scan data;

reconstructing sets of images, prospectively; and displaying images.

\* \* \* \* \*

UNITED STATES PATENT AND TRADEMARK OFFICE
CERTIFICATE OF CORRECTION

PATENT NO. : 6,141,398
DATED : October 31, 2000
INVENTOR(S) : Hui David He, Stanley H. Fox and Sholom M. Ackelsberg It is certified that error appears in the above-identified patent and that said Letters Patent is hereby corrected as shown below:

<u>Title page,</u>
Item [57], 12 lines below the heading "ABSTRACT", cancel "method, e.g.,".

Signed and Sealed this

Thirtieth Day of October, 2001

Attest:

*Nicholas P. Godici*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO. : 6,141,398
DATED : October 31, 2000
INVENTOR(S) : Hui David He, Stanley H. Fox, and Sholom M. Ackelsberg It is certified that error appears in the above-identified patent and that said Letters Patent is hereby corrected as shown below:

Title page, item [57],
Line 12, below the heading "ABSTRACT", cancel "method, e.g.,".

Signed and Sealed this

Sixth Day of November, 2001

Attest:

NICHOLAS P. GODICI
Attesting Officer   Acting Director of the United States Patent and Trademark Office